US011426721B2

(12) United States Patent
Nagaoka et al.

(10) Patent No.: US 11,426,721 B2
(45) Date of Patent: Aug. 30, 2022

(54) BUBBLE ELIMINATING STRUCTURE, BUBBLE ELIMINATING METHOD, AND AGITATING METHOD USING THE SAME

(71) Applicant: Hitachi High-Technologies Corporation, Tokyo (JP)

(72) Inventors: Yoshihiro Nagaoka, Tokyo (JP); Taro Nakazawa, Tokyo (JP); Mitsuhiro Miyazaki, Tokyo (JP); Ryusuke Kimura, Tokyo (JP); Motohiro Yamazaki, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 856 days.

(21) Appl. No.: 16/313,485

(22) PCT Filed: Jun. 26, 2017

(86) PCT No.: PCT/JP2017/023377
§ 371 (c)(1),
(2) Date: Dec. 27, 2018

(87) PCT Pub. No.: WO2018/020924
PCT Pub. Date: Feb. 1, 2018

(65) Prior Publication Data
US 2019/0314809 A1    Oct. 17, 2019

(30) Foreign Application Priority Data
Jul. 25, 2016  (JP) .............................. JP2016-145219

(51) Int. Cl.
*G01N 35/08* (2006.01)
*G01N 21/05* (2006.01)
(Continued)

(52) U.S. Cl.
CPC ......... *B01L 3/502* (2013.01); *B01L 3/502723* (2013.01); *B01L 3/567* (2013.01);
(Continued)

(58) Field of Classification Search
CPC ......... G01N 2021/054; G01N 35/1009; G01N 35/08; G01N 37/00; C12M 29/20;
(Continued)

(56) References Cited

U.S. PATENT DOCUMENTS

2007/0183935 A1* 8/2007 Clemmens ............. C12M 23/42
422/400
2011/0220502 A1    9/2011 Selden et al.
(Continued)

FOREIGN PATENT DOCUMENTS

EP          2042237 A1      4/2009
JP       2006-246777 A      9/2006
(Continued)

OTHER PUBLICATIONS

International Search Report of PCT/JP2017/023377 dated Sep. 12, 2017.

*Primary Examiner* — Dean Kwak
(74) *Attorney, Agent, or Firm* — Mattingly & Malur, PC

(57) ABSTRACT

Provided are a bubble eliminating structure and a bubble eliminating method which eliminate bubbles in a liquid by agitating the liquid, and an agitating method using the same. A first groove 114, which is an upstream bubble eliminating groove, and a second groove 131, which is a downstream bubble eliminating groove, are branched from a mixing well 13. After starting suction of the liquid from mixing well 13 into the first groove 114, suction of the liquid from the mixing well 13 into the second groove 131 is started, and after completion of discharge of the liquid from the first groove 114 into the mixing well 13, discharge of the liquid (Continued)

from the second groove 131 into the mixing well 13 is completed. This operation is repeated to eliminate bubbles.

8 Claims, 10 Drawing Sheets

(51) Int. Cl.
  *B01L 3/00* (2006.01)
  *G01N 37/00* (2006.01)
  *C12M 1/00* (2006.01)
(52) U.S. Cl.
  CPC ...... *G01N 35/08* (2013.01); *B01L 2200/0684* (2013.01); *B01L 2300/049* (2013.01); *B01L 2300/0636* (2013.01); *B01L 2300/0816* (2013.01); *B01L 2300/123* (2013.01); *B01L 2400/0481* (2013.01); *B01L 2400/0487* (2013.01); *B01L 2400/0666* (2013.01); *B01L 2400/086* (2013.01); *C12M 1/00* (2013.01); *C12M 29/20* (2013.01); *G01N 37/00* (2013.01); *G01N 2021/054* (2013.01)
(58) Field of Classification Search
  CPC .............. C12M 1/00; B01L 2200/0684; B01L 2300/123; B01L 2400/0481; B01L 2400/082; B01L 2300/049; B01L 2300/0636; B01L 2300/0816; B01L 2400/0487; B01L 2400/0666; B01L 2400/086; B01L 3/502; B01L 3/502723; B01L 3/567
  See application file for complete search history.

(56) References Cited

U.S. PATENT DOCUMENTS

| 2013/0171640 A1 | 7/2013 | Kwon et al. |
| 2015/0151295 A1 | 6/2015 | Kimura et al. |
| 2017/0138974 A1 | 5/2017 | Nakazawa et al. |

FOREIGN PATENT DOCUMENTS

| JP | 2014-018180 A | 2/2014 |
| JP | 2014-163713 A | 9/2014 |
| JP | 2016-005458 A | 1/2016 |
| WO | 2010/073020 A1 | 7/2010 |
| WO | 2015/186454 A1 | 12/2015 |

\* cited by examiner (A)

(B)

BUBBLE ELIMINATING STRUCTURE, BUBBLE ELIMINATING METHOD, AND AGITATING METHOD USING THE SAME

TECHNICAL FIELD

The present invention relates to a bubble eliminating structure, a bubble eliminating method, and an agitating method using the same.

BACKGROUND ART

PTL 1 describes a biochip for mixing liquid in a flow channel. PTL 1 describes, as reciprocal mixing of the polymerase chain reaction (hereinafter "PCR") solution, "the PCR solution is moved from the PCR reconstitution and reciprocation chamber back to the eluate metering chamber by linearly decreasing the pressure of drive line DL7 from 15 to 0 psig over 15 seconds. The air between the eluate and valve V13 is compressed and acts as an air spring to push against the PCR mixture moving it towards the metering chamber. The PCR mixture is reciprocally mixed by linearly increasing the pressure of the drive line DL7 from 0 to 15 psig over 15 seconds, and then linearly decreasing the pressure from 15 to 0 psig over 15 seconds". In addition, PTL 2 describes a biochemical reagents storage device capable of hermetically storing a small amount of reagents and dropping reagents from a storage section while preventing the reagents from being exposed to the air, and a biochemical analysis device using the biochemical reagents storage device. PTL 3 describes a liquid feed system and method for feeding microfluid.

CITATION LIST

Patent Literature

PTL 1: JP 2016-5458 A
PTL 2: International Patent Publication No. WO2015/186454
PTL 3: International Patent Publication No. WO2010/073020

SUMMARY OF INVENTION

Technical Problem

In the reciprocal mixing method described in PTL 1 described above, a liquid is simply caused to reciprocate from the reconstitution and reciprocation chamber of the PCR to the eluate metering chamber, so that bubbles in the liquid are not eliminated. In PTL 2, a device flow channel is sealed with a flow channel sealing pin that is caused to protrude from a holder and is displaced. Accordingly, the flow channel cannot be provided on the lower surface side of a biochip, which results in a complicated structure. PTL 3 discloses a structure in which grooves are continuously installed at three locations so as to cause a liquid to flow in one direction. However, PTL 3 fails to mention the elimination of bubbles.

An object of the present invention is to provide a bubble eliminating structure and a bubble eliminating method which are capable of eliminating bubbles in a liquid with a simple configuration, and an agitating method using the same.

Solution to Problem

To attain the above-described object, the present invention provides a bubble eliminating structure including an elastic membrane, an analysis chip installed on an upper surface side of the elastic membrane; and a driving portion installed on a lower surface side of the elastic membrane. The driving portion includes recesses being separated from each other by mounting the analysis chip on the driving portion through the elastic membrane. The analysis chip includes a vessel provided on the upper surface, a bubble eliminating groove, and a plurality of liquid delivery grooves, the bubble eliminating groove and the plurality of liquid delivery grooves being provided on the lower surface. The liquid delivery grooves are separated from each other by bringing the elastic membrane into close contact with the analysis chip. The bubble eliminating groove communicates with the vessel in a middle of the bubble eliminating groove. An end portion of the bubble eliminating groove is configured to communicate with the liquid delivery grooves through a gap between the analysis chip and the elastic membrane, the gap being generated when the elastic membrane is deformed in the recesses.

Further, to attain the above-described object, the present invention provides a bubble eliminating method using a bubble eliminating structure. The bubble eliminating structure includes an analysis chip installed on an upper surface side of an elastic membrane, and a driving portion installed on a lower surface side of the elastic membrane. The analysis chip includes a vessel provided on the upper surface, and a first groove and a second groove that are provided on the lower surface and are branched from the vessel. The bubble eliminating method includes starting suction of a liquid from the vessel into the second groove after starting suction of a liquid from the vessel into the first groove, and completing suction of a liquid from the second groove into the vessel after completion of discharge of a liquid from the first groove into the vessel.

Furthermore, to attain the above-described object, the present invention provides an agitating method for mixing a plurality of liquids, the agitating method including: branching a mixing vessel into a first groove and a second groove, and causing the plurality of liquids to be joined in the mixing vessel by using the first groove; starting suction of the liquids from the mixing vessel into the second groove after starting suction of the liquids joined from the mixing vessel into the first groove; and completing discharge of the liquids from the second groove into the mixing vessel after completion of discharge of the liquids from the first groove into the mixing vessel.

Advantageous Effects of Invention

According to the present invention, it is possible to provide a bubble eliminating structure and a bubble eliminating method which are capable of eliminating bubbles in a liquid with a simple configuration, and an agitating method using the same.

DESCRIPTION OF EMBODIMENTS

Figure 1:
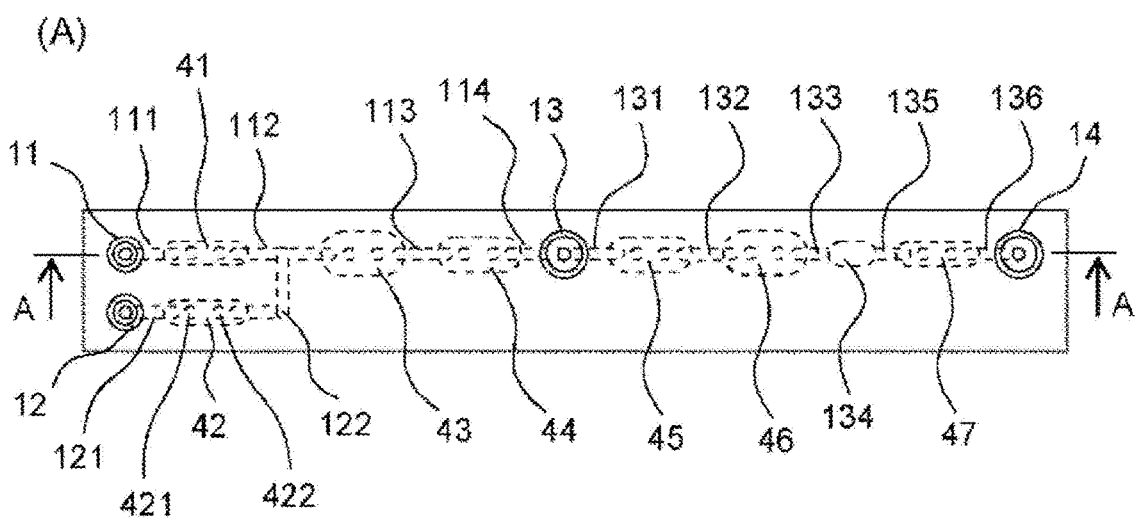
FIG. 1 illustrates a top view and a side sectional view of a bubble eliminating structure according to a first embodiment.
Figure 1:
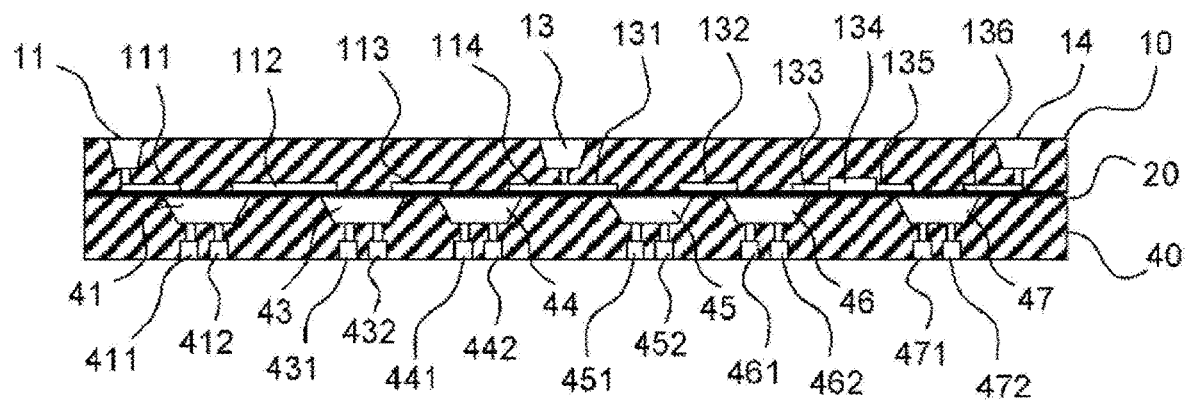

Various embodiments of the present invention will be described below with reference to the drawings.

First Embodiment

A bubble eliminating structure including an analysis chip, and a chemical analysis device according to a first embodiment will be described with reference to FIGS. 1 to 3. In this embodiment, a bubble eliminating structure and a bubble eliminating method for moving and mixing a liquid sample, such as blood, urine, or swab, and a reagent in the chemical analysis device and performing optical measurement for identification, quantitative determination, or the like on chemical substances, and an agitating method using the same will be described.

FIGS. 2(A) and 2(B) respectively illustrate a top view and a side view of the chemical analysis device according to the first embodiment. In the chemical analysis device illustrated in FIGS. 2(A) and 2(B), an analysis chip 10 and a membrane 20 in the bubble eliminating structure are pushed against a driving portion 40 by a lid 30. The lid 30 is rotatably supported around a rotary supporting portion 31. FIG. 2(A) illustrates a state where the lid 30 is halfway opened and the bubble eliminating structures including two analysis chips 10 are arranged side by side. FIG. 2(B) illustrates that the lid 30 is completely closed and is fastened to a housing 50 by a lock mechanism 51. The lid 30 is provided with an injection window 32 for injecting a sample and a reagent into the analysis chips 10, and an observation window 33 for observing the analysis result.

Below the housing 50, a control portion 60 for controlling an air pressure within a driving portion 40 is provided, and an air pipe 70 is connected to the control portion 60 from the driving portion 40. The operation of the control portion 60 is controlled by a signal from an operating portion 61 provided outside of the device.

FIGS. 1(A) and 1(B) respectively illustrate a top view and a side sectional view of the bubble eliminating structure consisting of an analysis chip, a membrane, and a driving portion according to the first embodiment. Specifically, the bubble eliminating structure includes an elastic membrane, an analysis chip installed on an upper surface side of the elastic membrane, and a driving portion installed on a lower surface side of the elastic membrane. The driving portion includes recesses that are separated from each other by mounting the analysis chip on the driving portion through the elastic membrane. The analysis chip includes a vessel provided on the upper surface, and a bubble eliminating groove and a plurality of liquid delivery grooves that are provided on the lower surface. The liquid delivery grooves are separated from each other by bringing the elastic membrane into close contact with the analysis chip. The bubble eliminating groove communicates with the vessel in the middle of the bubble eliminating groove. An end portion of the bubble eliminating groove is configured to communicate with the liquid delivery grooves through a gap between the analysis chip and the elastic membrane, the gap being generated when the elastic membrane is deformed in the recesses.

Figure 2:
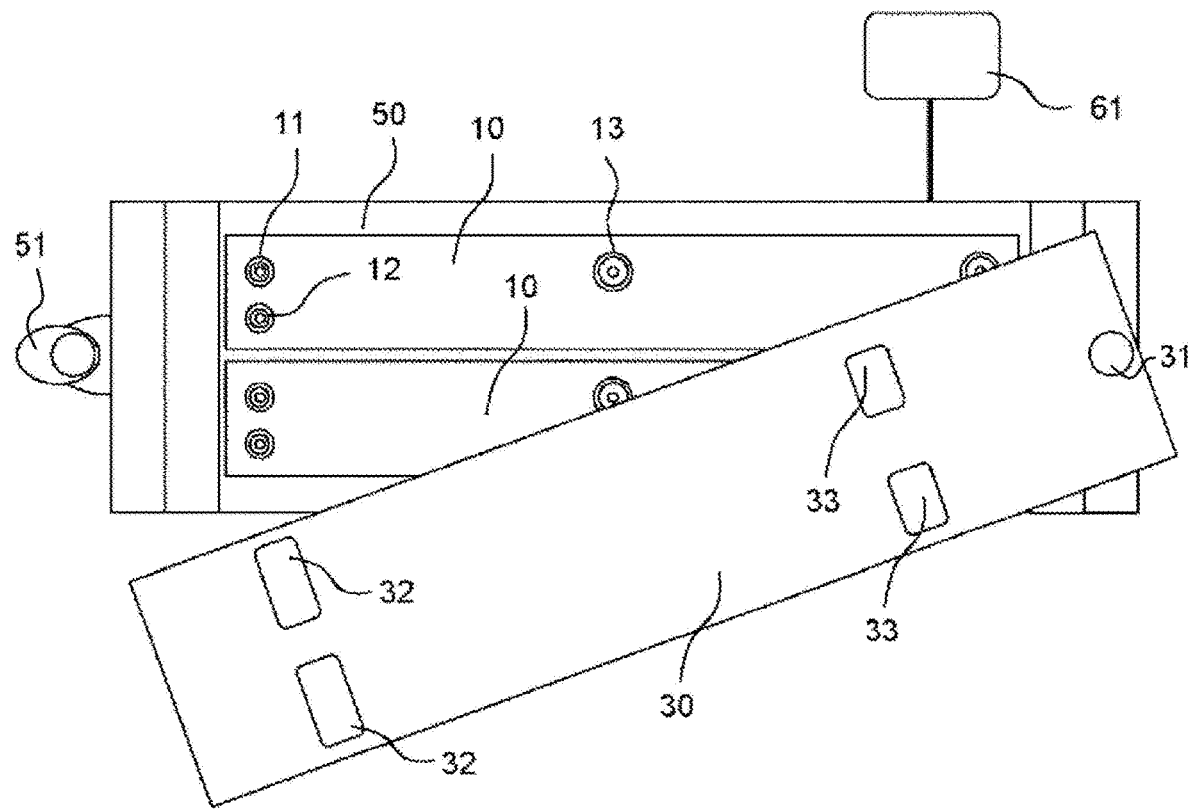
FIG. 2 illustrates a top view and a side view of a chemical analysis device according to the first embodiment.
Figure 2:
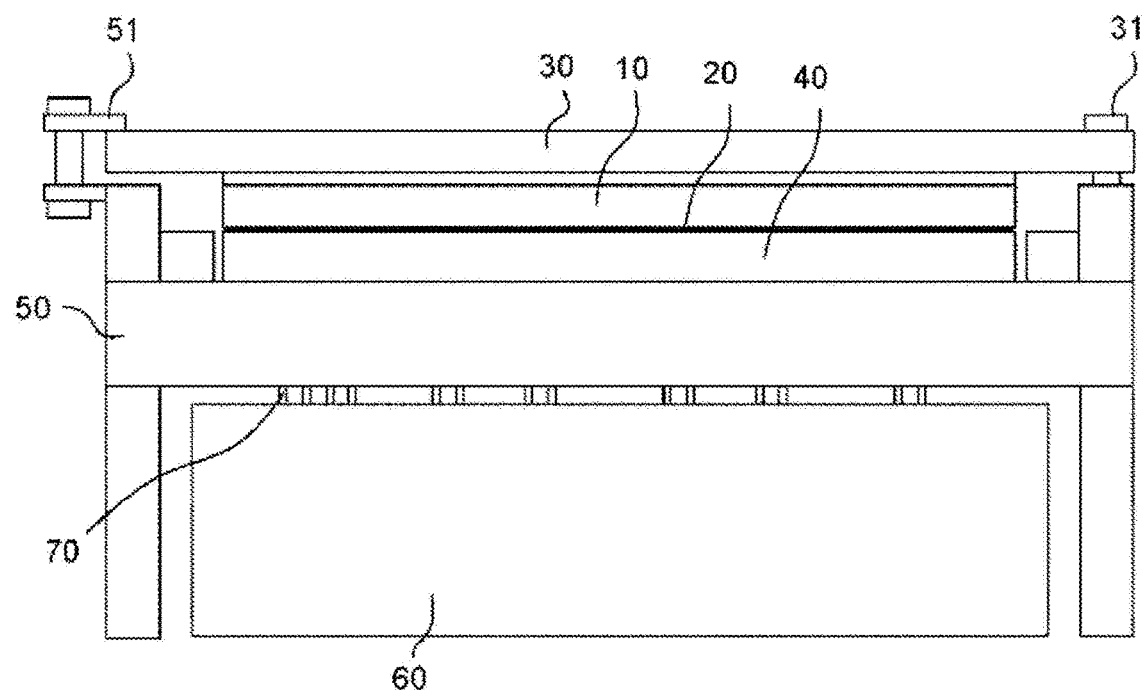

The bubble eliminating structure is mounted on the chemical analysis device illustrated in FIG. 2. FIG. 2(B) illustrates a state where the analysis chip 10, the membrane 20, and the driving portion 40 in the bubble eliminating structure are pushed by the lid 30. FIG. 1(A) is a view of the analysis chip 10 as viewed from the upper surface side. Each well serving as a vessel on the upper surface side of the analysis chip is indicated by a solid line. The grooves on the lower surface side of the analysis chip and the recesses in the driving portion 40 are each indicated by a broken line. FIG. 1(B) is a sectional view taken along a line A-A in FIG. 1(A). The analysis chip 10 and the driving portion 40 are in contact with each other through the membrane 20.

On the upper surface side of the analysis chip 10, a sample well 11, a reagent well 12, a mixing well 13, and a waste liquid well 14 are provided as vessels. On the lower surface side, a plurality of grooves 111, 112, 113, 114, 121, 122, 131, 132, 133, 134, 135, and 136 is provided. In the configuration according to this embodiment, the grooves 114 and 131 function as an upstream bubble eliminating groove and a downstream bubble eliminating groove, respectively, and the groove 134 functions as a processing groove. Unless otherwise stated, the other grooves function as liquid delivery grooves.

The membrane 20 is an elastic body formed of a high-molecular compound, such as rubber or resin. The membrane 20 is deformed by an air pressure to cause a fluid to move, and is brought into close contact with the surface of each of the analysis chip 10 and the driving portion 40, thereby sealing the fluid.

The driving portion 40 is provided with recesses 41, 42, 43, 44, 45, 46, and 47 on the upper surface side in close contact with the membrane 20. Two types of pipes, i.e., pressurizing pipes 411, 421, 431, 441, 451, 461, and 471 and decompression pipes 412, 422, 432, 442, 452, 462, and 472, are each connected to the air pipe 70 illustrated in FIG. 2 from the respective recesses.

Figure 3:
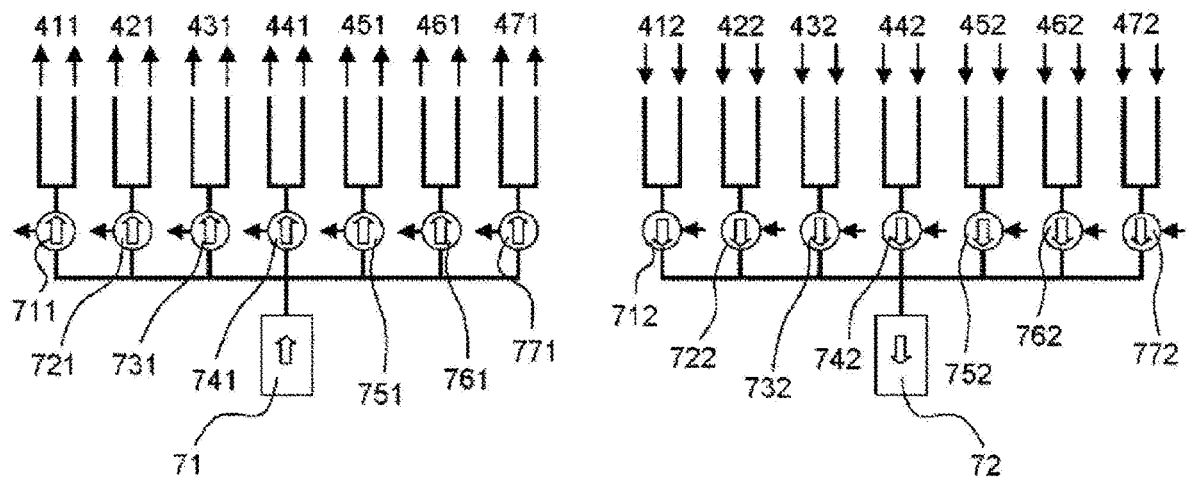
FIG. 3 illustrates an air pipeline diagram for controlling a pressure in a driving portion of the chemical analysis device according to the first embodiment.

FIG. 3 is an air pipeline diagram for controlling the pressure in the driving portion 40 according to this embodiment, and the air pipeline is installed in the control portion 60. The pressurizing pump 71 is branched into seven lines, which lead to pressurizing solenoid valves 711, 721, 731, 741, 751, 761, and 771, respectively, and are each further branched into two lines and connected to the pressurizing pipe of the driving portion 40. Two lines are branched from each of the pressurizing solenoid valves because the chemical analysis device according to this embodiment has two bubble eliminating structures mounted thereon as illustrated in FIG. 2(A). Similarly, the decompressing pump 72 is branched into seven lines, which lead to the decompressing solenoid valves 712, 722, 732, 742, 752, 762, and 772, respectively, and are each further branched into two lines and connected to the decompression pipe of the driving portion 40.

At the time of energization, the pressurizing solenoid valve 711 and the like communicate with an air pipe leading from the pump 71 to the driving portion 40, and the recess 41 and the like in the driving portion 40 are pressurized. On the other hand, at the time of non-energization, the air pipe provided on the pump 71 side is closed, thereby allowing a liquid to flow out of the air pipe provided on the driving portion 40 side, i.e., to flow out into the atmosphere, while preventing a liquid from flowing into the air pipe from the outside.

At the time of energization, the decompressing solenoid valve 712 and the like communicate with an air pipe leading from the pump 72 to the driving portion 40, and the recess 41 and the like in the driving portion 40 are decompressed. On the other hand, at the time of non-energization, the air pipe provided on the pump 72 side is closed, thereby allowing a liquid to flow into the air pipe provided on the driving portion 40 side from the atmosphere, while preventing a liquid from flowing to the outside from the air pipe.

Figure 4:
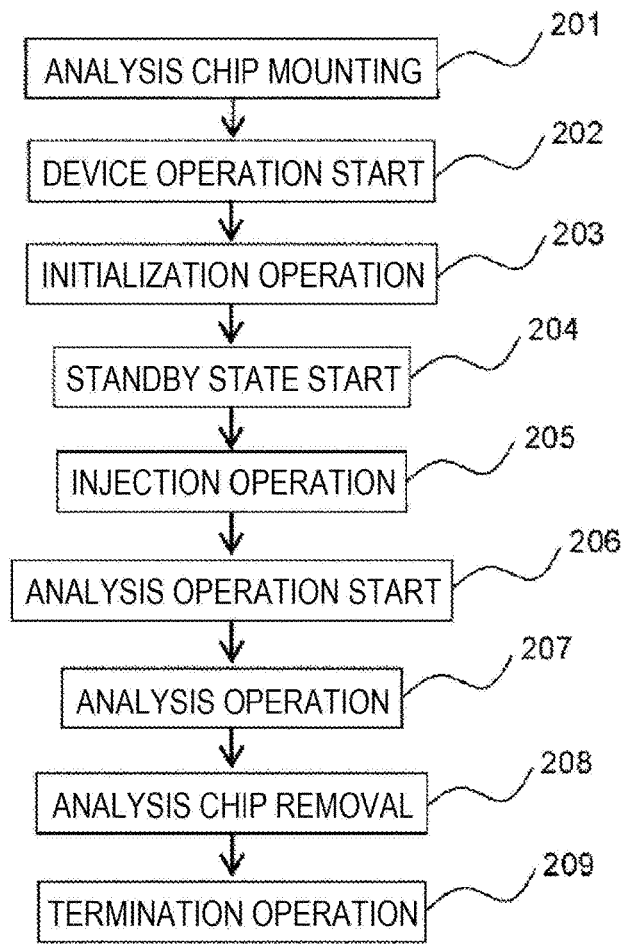
FIG. 4 is a flowchart illustrating an operation flow of the chemical analysis device according to the first embodiment.

Operations for the bubble eliminating structure and the chemical analysis device according to this embodiment will be described below with reference to an operation flow illustrated in FIG. 4. Before an operation is started, the driving portion 40 is installed in the chemical analysis device and the air pipe 70 is connected. In an analysis chip mounting 201, which is a first operation, an operator mounts the analysis chip 10 and the membrane 20 on the driving portion 40 and closes the lid 30. As described above, this state is illustrated in FIG. 2(B). Note that the analysis chip 10 and the membrane 20 are normally integrated together and packaged. The packaged analysis chip and membrane are mounted on the driving portion 40.

In the subsequent step of device operation start 202, the operator selects a control procedure depending on the analysis content from the operating portion 61, and starts a device operation. The chemical analysis device starts an initialization operation 203, and performs an operation of opening or closing solenoid valves, pressurization and decompression operations using pumps, and, as needed, checking of a pressure, and the like.

After that, all the decompressing solenoid valve 712 and the like are closed in a state where the pressurizing pump 71 and the decompressing pump 72 are operated, and the step of standby state start 204 is carried out in a state where at least the pressurizing solenoid valves 711 and 721 are opened.

In a standby state, in an injection operation 205, the operator injects a sample into the sample well 11 from the injection window 32, and also injects a reagent into the reagent well 12 from the injection window 32. At this time, since the pressurizing solenoid valves 711 and 712 are opened, the recesses 41 and 42 are pressurized and the membrane 20 is pushed against the lower surface of the analysis chip in each recess. Accordingly, the grooves 111 and 121 are sealed, which prevents the sample and the reagent from flowing out of the sample well 11 and the reagent well 12, respectively.

After completion of injection of the sample and the reagent, the operator issues an instruction for analysis operation start 206 from the operating portion 61, and the chemical analysis device carries out an analysis operation 207. After the analysis is finished, the analysis result is stored in a memory within the chemical analysis device, and is displayed, as needed, on a display or the like of the operating portion 61.

After the analysis operation 207 is finished, in analysis chip removal 208, the operator removes the analysis chip 10 and the membrane 20 and stores or discards them. If there is another analysis to be subsequently conducted, the processing returns to the analysis chip mounting 201, and a new analysis chip is mounted to carry out the analysis. If there is no other analysis, the operator performs a termination operation 209 using the operating portion 61, and stops the device.

Figure 5:
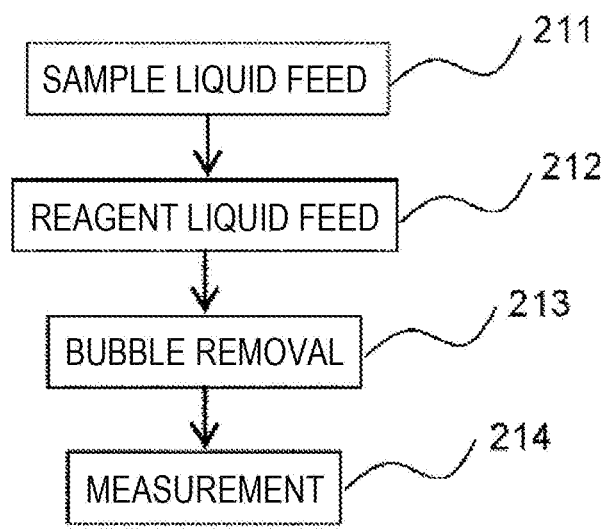
FIG. 5 is a flowchart illustrating an analysis operation flow of the chemical analysis device according to the first embodiment.

Referring next to FIG. 5, the analysis operation 207 of the chemical analysis device according to this embodiment will be described in detail. In the sample liquid feed 211 illustrated in FIG. 5, the sample held in the sample well 11 is fed to the mixing well 13. A specific liquid feed method will be described with reference to FIGS. 6 and 7.

Figure 6:
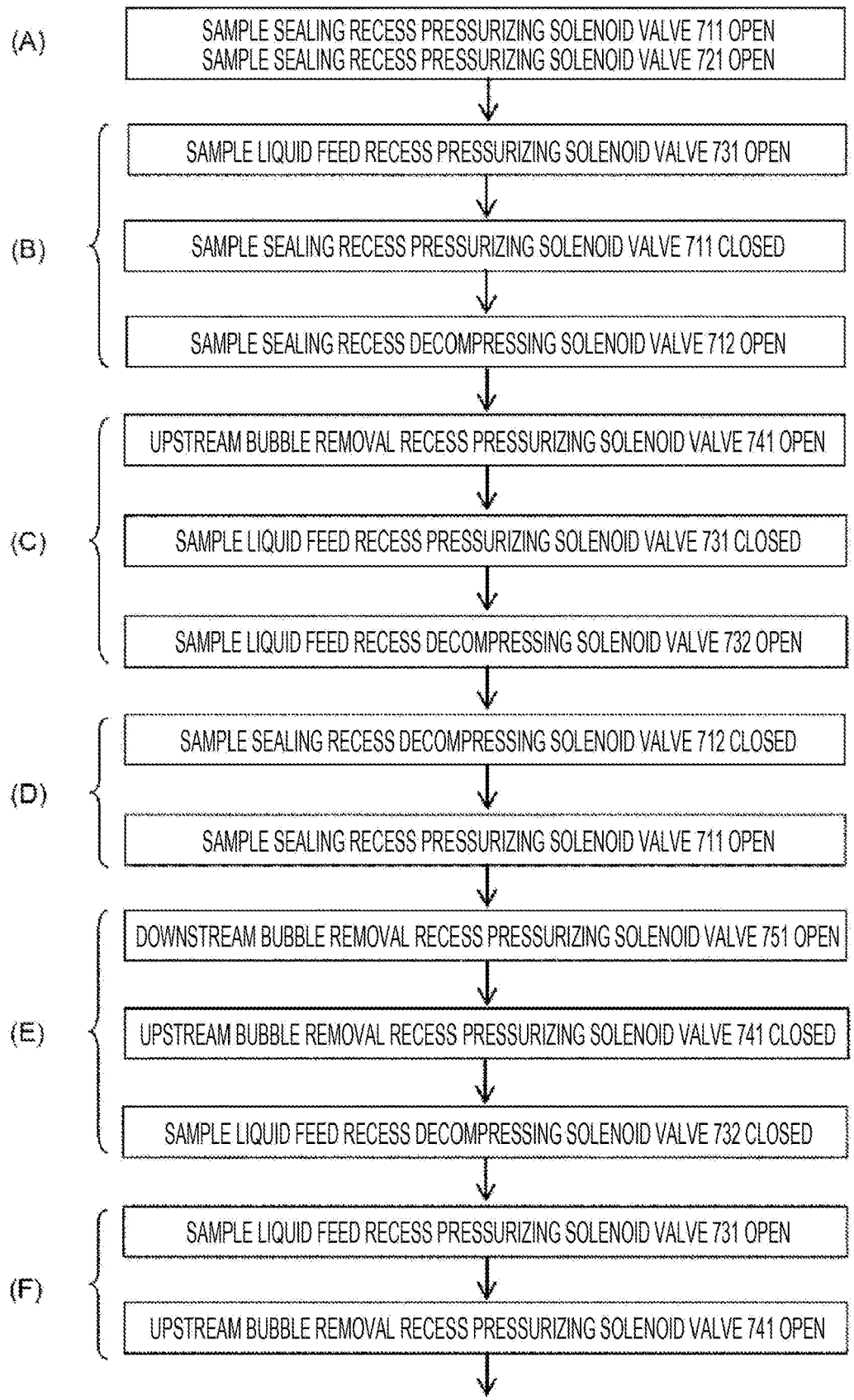
FIG. 6 is a flowchart illustrating a liquid feed operation flow of the chemical analysis device according to the first embodiment.
Figure 7:
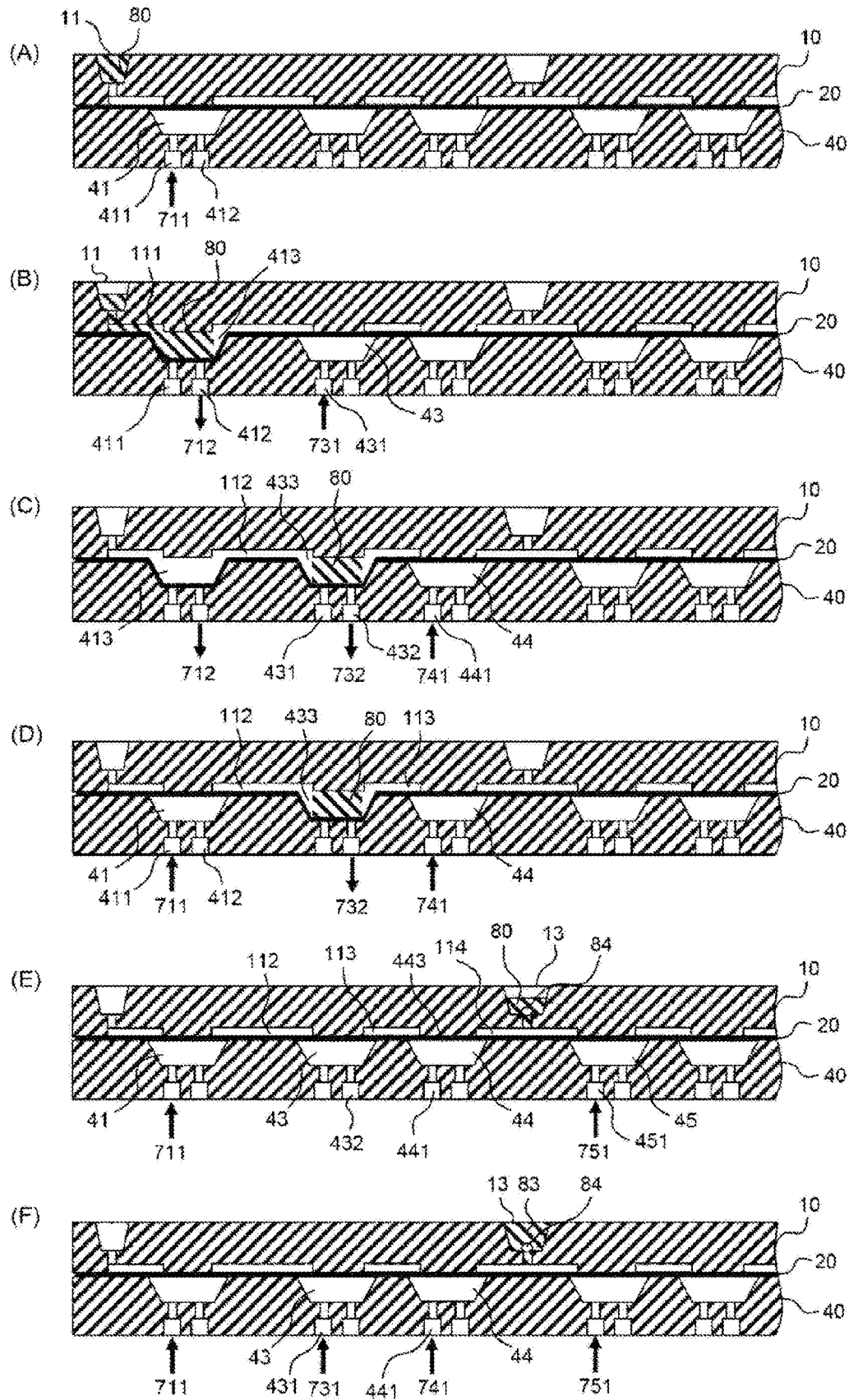
FIG. 7 is an explanatory diagram illustrating a liquid feed operation of the chemical analysis device according to the first embodiment.

FIG. 6 is a flowchart illustrating a liquid feed operation flow by controlling opening/closing of the pressurizing solenoid valves and decompressing solenoid valves in the chemical analysis device according to this embodiment. FIG. 7 is an explanatory diagram illustrating the liquid feed operation. Note that solid-line arrows illustrated in FIG. 7 indicate that the solenoid valves respectively corresponding to the pressurizing pipes and decompression pipes are opened, upward arrows indicate that the pressurizing solenoid valves are opened to pressurize the recesses, and downward arrows indicate that the decompressing solenoid valves are opened to decompress the recesses.

FIG. 6(A) and FIG. 7(A) illustrate a state at the time of the above-described analysis operation start, and a sample 80 is held in the sample well 11. Specifically, in FIG. 7(A), the sample sealing recess pressurizing solenoid valve 711 is opened. Accordingly, air is flown from a sample sealing recess pressurizing pipe 411, so that the sample sealing recess 41, which is a fourth recess, is pressurized and the sample sealing recess decompressing solenoid valve 712 provided on the sample sealing recess decompression pipe 412 side is closed. Although not illustrated, the reagent is held in the reagent well 12 and the reagent sealing recess pressurizing solenoid valve 721 is also opened, so that the reagent sealing recess 42, which is the fourth recess, is pressurized.

Next, as illustrated in FIG. 6(B) and FIG. 7(B), the sample liquid feed recess pressurizing solenoid valve 731 is opened to allow air to flow from the sample liquid feed recess pressurizing pipe 431, and the sample liquid feed recess 43, which is a third recess, is pressurized. Further, the sample sealing recess pressurizing solenoid valve 711 is closed to stop the in-flow of air from the sample sealing recess pressurizing pipe 411, and the sample sealing recess decompressing solenoid valve 712 is opened to allow air to flow out of the sample sealing recess decompression pipe 412, thereby decompressing the sample sealing recess 41. At this time, the membrane 20 is drawn to a bottom surface of the sample sealing recess 41. Accordingly, a sample sealing portion gap 413 is generated between the membrane 20 and the analysis chip 10, and the sample 80 is drawn into the sample sealing portion gap 413 through the liquid delivery groove 111, which is a sample upstream groove, from the sample well 11.

Next, as illustrated in FIG. 6(C) and FIG. 7(C), the upstream bubble removal recess pressurizing solenoid valve 741 is opened while the sample sealing recess decompressing solenoid valve 712 remains open, air is allowed to flow from the upstream bubble removal recess pressurizing pipe 441 to pressurize the upstream bubble removal recess 44, which is a first recess, and the sample liquid feed recess pressurizing solenoid valve 731 is closed to stop the in-flow of air from the sample liquid feed recess pressurizing pipe 431. Further, the sample liquid feed recess decompressing solenoid valve 732 is opened to allow air to flow out of the sample liquid feed recess decompression pipe 432 to decompress the sample liquid feed recess 43 which is the third recess. At this time, since the membrane 20 is drawn to a bottom surface of the sample liquid feed recess 43, a sample sealing portion gap 433 is generated between the membrane 20 and the analysis chip 10, and the sample 80 is drawn into the sample sealing portion gap 433 through the liquid delivery groove 112, which is a sample sucking groove, from the sample sealing portion gap 413.

Next, as illustrated in FIG. 6(D) and FIG. 7(D), the sample sealing recess decompressing solenoid valve 712 is closed while the upstream bubble removal recess pressurizing solenoid valve 741 and the sample liquid feed recess decompressing solenoid valve 732 remain open, thereby stopping the out-flow of air from the sample sealing recess decompression pipe 412. Further, the sample sealing recess pressurizing solenoid valve 711 is opened to allow the air to flow in from the sample sealing recess pressurizing pipe 411 and the sample sealing recess 41 is pressurized. At this time, the sample sealing recess 41 and the upstream bubble removal recess 44 are pressurized, so that the liquid delivery groove 112, which is the sample sucking groove, and the liquid delivery groove 113, which is a sample discharge groove, are sealed and the sample 80 is held in the sample sealing portion gap 433.

Next, as illustrated in FIG. 6(E) and FIG. 7(E), the downstream bubble removal recess pressurizing solenoid valve 751 is opened while the sample sealing recess pressurizing solenoid valve 711 remains open, thereby allowing the air to flow in from the downstream bubble removal recess pressurizing pipe 451 and pressurizing the downstream bubble removal recess 45 which is a second recess. The upstream bubble removal recess pressurizing solenoid valve 741 is closed to stop the in-flow of air from the upstream bubble removal recess pressurizing pipe 441. The sample liquid feed recess decompressing solenoid valve 732 is closed to stop the out-flow of air from the sample liquid feed recess decompression pipe 432. At this time, the membrane 20 is to be returned to its original state by an elastic force and is to push the sample 80 out of the sample sealing portion gap 433. However, the liquid delivery groove 112, which is the sample sucking groove, is sealed by pressurization of the sample sealing recess 41, which is the fourth recess, thereby preventing a liquid from flowing out. On the other hand, the liquid delivery groove 113, which is the sample discharge groove, is not sealed because the pressurization of the upstream bubble removal recess 44 is stopped. Accordingly, the sample 80 can flow out. Specifically, the sample 80 flows into an upstream bubble removing portion gap 443 between the analysis chip 10 and the membrane 20 of the upstream bubble removal recess 44 from the sample sealing portion gap 433 through the sample discharge groove 113, and flows out into the mixing well 13 from the upstream bubble eliminating groove 114. Bubbles 84 in the mixing well 13 will be described below.

Next, as illustrated in FIG. 6(F) and FIG. 7(F), the sample liquid feed recess pressurizing solenoid valve 731 and the upstream bubble removal recess pressurizing solenoid valve 741 are opened while the sample sealing recess pressurizing solenoid valve 711 and the downstream bubble removal recess pressurizing solenoid valve 751 remain open, thereby allowing the air to flow in from the sample liquid feed recess pressurizing pipe 431 and the upstream bubble removal recess pressurizing pipe 441, and pressurizing the sample liquid feed recess 43, which is the third recess, and the upstream bubble removal recess 44 which is the first recess. At this time, the sample sealing portion gap 433 and the upstream bubble removing portion gap 443 are completely closed, and the entire sample 80 flows out into the mixing well 13.

The operation of the sample liquid feed 211 illustrated in FIG. 5, i.e., the operation of feeding the sample 80 held in the sample well 11 into the mixing well 13 has been described above.

Next, a reagent liquid feed 212 is carried out in the chemical analysis device. The liquid feed operation of feeding a reagent is substantially the same as the liquid feed operation of feeding a sample as described above. In this operation, the sample well 11 is replaced by the reagent well 12; the liquid delivery groove 111, which is the sample upstream groove, is replaced by the liquid delivery groove 121 which is a reagent upstream groove; the sample sealing recess 41 is replaced by the reagent sealing recess 42; the liquid delivery groove 112, which is the sample sucking groove, is replaced by the liquid delivery groove 122, which is a reagent suction groove; the sample sealing recess pressurizing pipe 411 is replaced by the reagent sealing recess pressurizing pipe 421; the sample sealing recess decompression pipe 412 is replaced by the reagent sealing recess decompression pipe 422; the sample sealing recess pressurizing solenoid valve 711 is replaced by the reagent sealing recess pressurizing solenoid valve 721; and the sample sealing recess decompressing solenoid valve 712 is replaced by the reagent sealing recess decompressing solenoid valve 722. It can be said that FIG. 7(F) also illustrates a state where the liquid feed operations for feeding the sample and the reagent are completed and a mixture 83 of the sample and the reagent is held in the mixing well 13.

In FIG. 6 and FIG. 7, the entire sample and reagent are moved into the mixing well 13, but instead, the amount of sample and reagent that is less than the amount of sample and reagent to be injected into the sample well 11 or the reagent well 12 can be moved into the mixing well 13, and the liquid can remain in the sample well 11 or the reagent well 12. The amount of liquid to be fed is substantially equal to the volume of the sample liquid feed recess 43. Accordingly, if the amount of liquid to be injected is more than the volume, the liquid remains in each well. Thus, if the amount of sample and reagent that is greater than or equal to the amount of sample and reagent required for analysis can be used, the operation in which the liquid remains in each well can also be employed.

However, in general, the amount of sample and reagent is small, and a wasteful amount of liquid that is not used for analysis is desirably eliminated. Accordingly, it is desirable to feed the total amount of injected liquid as illustrated in FIG. 7. In the case of feeding the total amount of liquid, the liquid is pushed out by air, and as illustrated in FIG. 7(E) or 7(F), the bubbles 84 are mixed in the mixing well 13. If an optical measurement is carried out in the state where the bubbles 84 are mixed, accurate measurement values cannot be obtained.

Accordingly, in the bubble eliminating structure and the chemical analysis device according to this embodiment, a bubble removing operation to be described below in bubble removal 213 illustrated in FIG. 5 is carried out.

The bubble removing operation using the configuration according to this embodiment will be described with reference to FIGS. 8 and 9. Specifically, as described above, the bubble eliminating structure includes the analysis chip installed on the upper surface side of the elastic membrane, and the driving portion installed on the lower surface side of the elastic membrane. The analysis chip includes the vessel provided on the upper surface, the first groove, which is provided on the lower surface and corresponds to the upstream bubble eliminating groove branched from the vessel, and the second groove, which is provided on the lower surface and corresponds to the downstream bubble eliminating groove. A bubble eliminating method in which the suction of a liquid from the vessel into the second groove is started after starting the suction of a liquid from the vessel into the first groove, and the discharge of a liquid from the second groove into the vessel is completed after completion of discharge of a liquid from the first groove into the vessel will be described.

Figure 8:
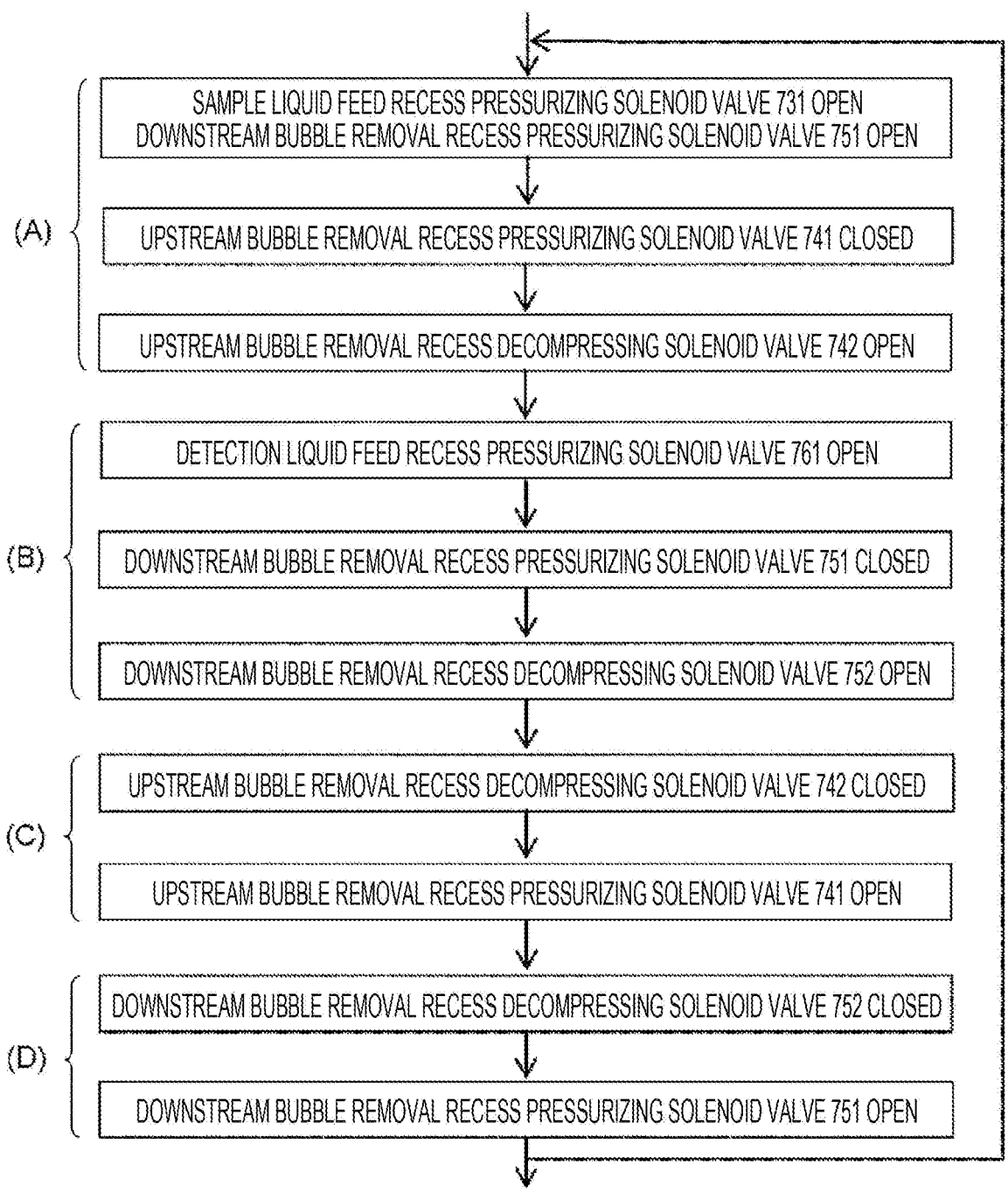
FIG. 8 is a flowchart illustrating a bubble removing operation flow of the chemical analysis device according to the first embodiment.

FIG. 8 is a flowchart illustrating a bubble removing operation flow of the chemical analysis device according to this embodiment. FIG. 9 is an explanatory diagram illustrating the bubble removing operation of the chemical analysis device according to this embodiment. The bubble removing operation according to this embodiment uses the bubble eliminating structure in which the upstream bubble removal recess 44, which is the first recess, the vessel, which is the mixing well 13, the downstream bubble removal recess 45, which is the second recess, and the like are connected with the upstream bubble eliminating groove 114 and the downstream bubble eliminating groove 131 through the membrane 20. After the decompression of the upstream bubble removal recess 44, which is the first recess, is started, the decompression of the downstream bubble removal recess 45, which is the second recess, is started. Then, after the decompression of the first recess is stopped, or the pressurization of the first recess is started, the decompression of the second recess is stopped, or the pressurization of the second recess is started. In the manner as described above, the bubble eliminating operation is carried out.

Figure 9:
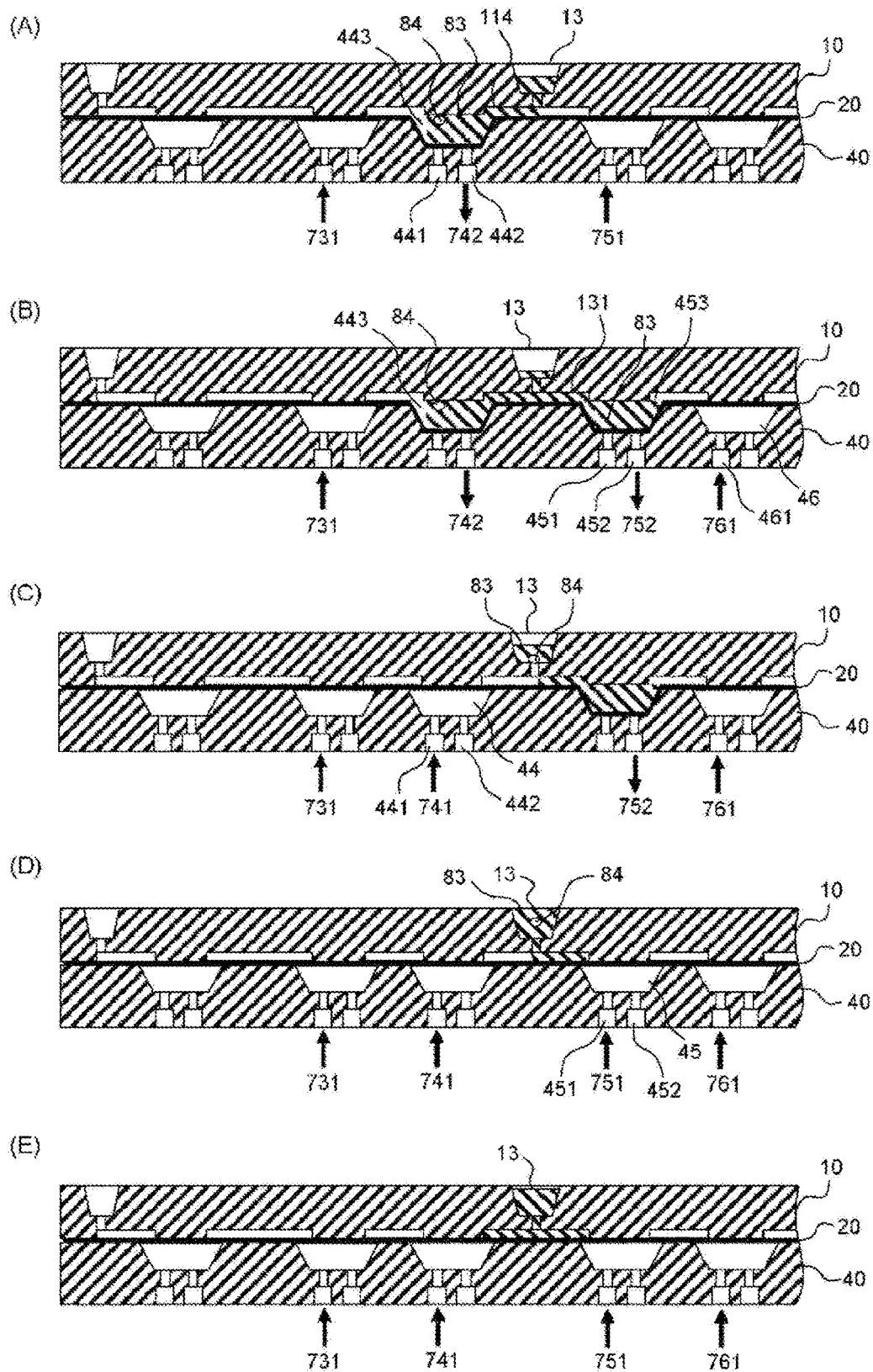
FIG. 9 is an explanatory diagram illustrating a bubble removing operation of the chemical analysis device according to the first embodiment.

FIG. 9(A) illustrates an operation to follow the state in which the liquid feed operation for the sample and the reagent illustrated in FIG. 7(F) is completed, and then the mixture 83 of the sample and the reagent is held in the mixing well 13. As illustrated in FIG. 8(A) and FIG. 9(A), the upstream bubble removal recess pressurizing solenoid valve 741 is closed while the sample liquid feed recess pressurizing solenoid valve 731 and the downstream bubble removal recess pressurizing solenoid valve 751 remain open, thereby stopping the in-flow of air from the upstream bubble removal recess pressurizing pipe 441. Next, the upstream bubble removal recess decompressing solenoid valve 742 is opened, thereby causing the air to flow out of the upstream bubble removal recess decompression pipe 442 and decompressing the upstream bubble removal recess 44. At this time, the membrane 20 is drawn to the bottom surface of the upstream bubble removal recess 44. Accordingly, the upstream bubble removing portion gap 443 is generated between the membrane 20 and the analysis chip 10, and the mixture 83 is drawn into the upstream bubble removing portion gap 443 from the mixing well 13 through the upstream bubble eliminating groove 114. Along with the movement of the mixture 83, the bubbles 84 in the bottom surface portion of the mixing well 13 illustrated in FIG. 7(F) move to the upstream bubble removing portion gap 443. Note that the sample sealing recess pressurizing solenoid valve 711 in the open state illustrated in FIG. 7(F) is irrelevant to the bubble removing operation. Accordingly, the sample sealing recess pressurizing solenoid valve may be in the open state or the closed state. FIG. 9 illustrates the closed state.

Next, as illustrated in FIG. 8(B) and FIG. 9(B), the pressurizing solenoid valve 761 for the processing liquid feed recess 46, which is a fifth recess, is opened while the sample liquid feed recess pressurizing solenoid valve 731 and the upstream bubble removal recess decompressing solenoid valve 742 remain open, thereby causing the air to flow in from the processing liquid feed recess pressurizing pipe 461 and pressurizing the processing liquid feed recess 46. The downstream bubble removal recess pressurizing solenoid valve 751 is closed, thereby stopping the in-flow of air from the downstream bubble removal recess pressurizing pipe 451. The downstream bubble removal recess decompressing solenoid valve 752 is opened, thereby causing air to flow out of the downstream bubble removal recess decompression pipe 452, and decompressing the downstream bubble removal recess 45 which is the second recess. At this time, since the membrane 20 is drawn to the bottom surface of the downstream bubble removal recess 45, the downstream bubble removing portion gap 453 is generated between the membrane 20 and the analysis chip 10, and the mixture 83 is drawn into the downstream bubble removing portion gap 453 from the mixing well 13 through the downstream bubble eliminating groove 131.

Next, as illustrated in FIG. 8(C) and FIG. 9(C), the upstream bubble removal recess decompressing solenoid valve 742 is closed while the sample liquid feed recess pressurizing solenoid valve 731, the downstream bubble removal recess decompressing solenoid valve 752, and the processing liquid feed recess pressurizing solenoid valve 761 remain open, thereby stopping the out-flow of air from the upstream bubble removal recess decompression pipe 442. The upstream bubble removal recess pressurizing solenoid valve 741 is opened, thereby causing the air to flow in from the upstream bubble removal recess pressurizing pipe 441, and pressurizing the upstream bubble removal recess 44 which is the first recess. At this time, the mixture 83 drawn into the upstream bubble removing portion gap 443 in FIG. 9(A) returns to the mixing well 13 through the upstream bubble eliminating groove 114, and the bubbles 84 also return to the same position, i.e., the bottom surface portion of the mixing well 13.

Next, as illustrated in FIG. 8(D) and FIG. 9(D), the downstream bubble removal recess decompressing solenoid valve 752 is closed while the sample liquid feed recess pressurizing solenoid valve 731, the upstream bubble removal recess pressurizing solenoid valve 741, and the processing liquid feed recess pressurizing solenoid valve 761 remain open, thereby stopping the out-flow of air from the downstream bubble removal recess decompression pipe 452. The downstream bubble removal recess pressurizing solenoid valve 751 is opened, thereby causing the air to flow in from the downstream bubble removal recess pressurizing pipe 451, and pressurizing the downstream bubble removal recess 45 which is the second recess. At this time, the mixture 83 drawn into the downstream bubble removing portion gap 453 in FIG. 9(B) returns to the mixing well 13 through the downstream bubble eliminating groove 131, and pushes the bubbles 84, which has returned to the bottom surface portion of the mixing well 13 in FIG. 9(C), up to the upper portion of the mixing well 13.

The operation illustrated in FIGS. 9(A) to 9(D) corresponds to one bubble removing operation, and this operation is repeated a plurality of times. If bubbles move to the upper portion of the mixing well 13, the bubbles are more likely to rise due to buoyancy and then disappear at a gas-liquid interface. If bubbles are present at the bottom surface portion of the mixing well 13, the bubbles are adsorbed to a solid wall, and thus the bubbles are less likely to rise due to buoyancy.

Accordingly, the bubbles at the bottom surface portion of the mixing well 13 are moved to the upstream bubble removing portion gap 443 via the upstream bubble eliminating groove 114 at one end, together with the mixture in the vicinity of the bottom surface portion. Then, when the mixture located at the upper portion of the mixing well 13 is moved to the downstream bubble removing portion gap 453 via the downstream bubble eliminating groove 131 to return the mixture to the mixing well 13, first, the mixture in the upstream bubble removing portion gap 443 is returned via the upstream bubble eliminating groove 114, so that the bubbles are returned to the bottom surface portion of the mixing well 13. Next, the mixture in the downstream bubble removing portion gap 453 is returned via the downstream bubble eliminating groove 131, thereby pushing the bubbles up to the upper portion of the mixing well 13. By repeating the above-described operation a plurality of times, as illustrated in FIG. 9(E), when the bubbles move to the upper portion of the mixing well 13, the bubbles gradually rise to the gas-liquid interface due to buoyancy and disappear.

Note that when the mixture is returned to the mixing well 13 from the gaps 443 and 453, the decompressing solenoid valve 742 or 752 is closed to pressurize the recesses 44 and 45 and cause the mixture to flow out into the mixing well 13. Further, the pressurizing solenoid valve 741 or 751 is opened to accelerate the pressurization of the recesses 44 and 45 and increase the outlet velocity of the mixture into the mixing well 13. Therefore, the bubbles are more likely to be removed.

The operation of the bubble removal 213 illustrated in FIG. 5 in the chemical analysis device according to this embodiment has been described above. Note that when this bubble removing operation is carried out, the mixture 83 moves in a reciprocating motion in the mixing well 13 and two gaps, i.e., the upstream bubble removing portion gap 443 and the downstream bubble removing portion gap 453, so that the liquid is agitated. In other words, the bubble removing operation in the configuration according to this embodiment also functions as an agitating operation. Accordingly, when a sample and a reagent are more likely to be mixed together, several times of bubble removing operations are sufficient to eliminate bubbles. However, if a sample and a reagent are less likely to be mixed together, several times of bubble removing operations required for sufficient agitation may be repeated to agitate the mixture. On the other hand, the operation illustrated in FIG. 9 corresponds to the operation of agitating the mixture 83 of the sample and the reagent, and bubbles are eliminated in the first several times of operations.

As indicated by measurement 214 in FIG. 5, a measurement operation is carried out after the bubble removing operation. The measurement operation includes processing such as feeding of the mixture 83 held in the mixing well 13 into the processing groove 134 illustrated in FIG. 1 after the bubble removing operation, and an optical measurement. The liquid feed operation is the same as the operation described above with reference to FIG. 7, and the measurement operation will be described with reference to an operation flow illustrated in FIG. 10 and FIG. 1.

Figure 10:
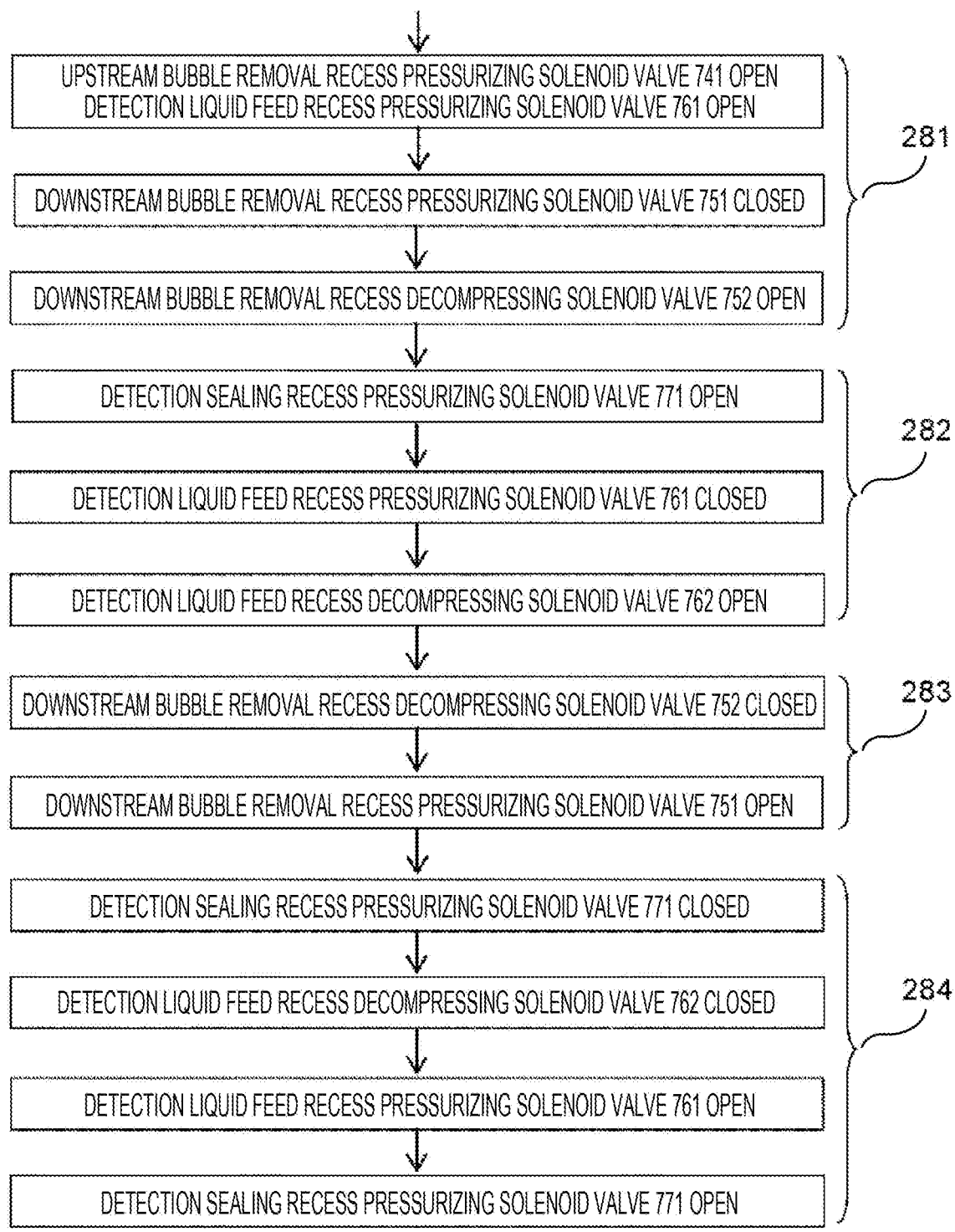
FIG. 10 is a flowchart illustrating a measurement operation flow of the chemical analysis device according to the first embodiment.

FIG. 10 is a flowchart illustrating a measurement operation flow of the chemical analysis device according to this embodiment. An operation 281 is subsequent to the operation illustrated in FIG. 9(E). The downstream bubble removal recess pressurizing solenoid valve 751 is closed while the upstream bubble removal recess pressurizing solenoid valve 741 and the processing liquid feed recess pressurizing solenoid valve 761 remain open, thereby stopping the in-flow of air from the downstream bubble removal recess pressurizing pipe 451. Next, the downstream bubble removal recess decompressing solenoid valve 752 is opened, thereby causing the air to flow out of the downstream bubble removal recess decompression pipe 452, and decompressing the downstream bubble removal recess 45. At this time, the membrane 20 is drawn to the bottom surface of the downstream bubble removal recess 45. As a result, a gap is generated between the membrane 20 and the analysis chip 10, and the mixture 83 is drawn into the gap from the mixing well 13 through the downstream bubble eliminating groove 131.

In an operation 282, the processing sealing recess pressurizing solenoid valve 771 is opened, thereby causing air to flow in from the processing sealing recess pressurizing pipe 471, and pressurizing the processing sealing recess 47 which is a sixth recess illustrated in FIG. 1. The processing liquid feed recess pressurizing solenoid valve 761 is closed, thereby stopping the in-flow of air from the processing liquid feed recess pressurizing pipe 461. Next, the processing liquid feed recess decompressing solenoid valve 762 is opened, thereby causing air to flow out of the processing liquid feed recess decompression pipe 462, and decompressing the processing liquid feed recess 46 which is the fifth recess. At this time, the membrane 20 is drawn to the bottom surface of the processing liquid feed recess 46. As a result, a gap is generated between membrane 20 and the analysis chip 10, and the mixture 83 is drawn into the gap of the processing liquid feed recess 46 from the mixing well 13 through the gap generated in the downstream bubble removal recess 45 and the processing suction groove 132.

In an operation 283, the downstream bubble removal recess decompressing solenoid valve 752 is closed while the processing liquid feed recess decompressing solenoid valve 762 and the processing sealing recess pressurizing solenoid valve 771 remain open, thereby stopping the out-flow of air from the downstream bubble removal recess decompression pipe 452. The downstream bubble removal recess pressurizing solenoid valve 751 is opened, thereby causing air to flow in from the downstream bubble removal recess pressurizing pipe 451, and pressurizing the downstream bubble removal recess 45. At this time, the membrane 20 closes and seals the gap generated in the downstream bubble removal recess 45 to return the mixture 83 to the mixing well 13.

In an operation 284, the processing sealing recess pressurizing solenoid valve 771 is closed while the downstream bubble removal recess pressurizing solenoid valve 751 remains open, thereby stopping the in-flow of air from the processing sealing recess pressurizing pipe 471, and the processing liquid feed recess decompressing solenoid valve 762 is closed to stop the out-flow of air from the processing liquid feed recess decompression pipe 462.

At this time, the membrane 20 is to be returned to its original state by an elastic force. The gap generated in the processing liquid feed recess 46, which is the fifth recess, is closed and the mixture 83 is filled in the liquid delivery groove 133, which is a processing liquid feed groove, the processing groove 134, and the processing discharge groove 135. An excess liquid passes through the space between the analysis chip 10 and the membrane 20 of the processing sealing recess 47, which is the sixth recess, and flows out into the waste liquid well 14 illustrated in FIG. 1 through the waste liquid groove 136. In this state, the processing groove 134 is irradiated with observation light from the observation window 33 illustrated in FIG. 2, and data is obtained. The analysis operation 207 according to this embodiment illustrated in FIG. 4 has been described above.

Note that the processing groove 134 has a function for holding a liquid in a hermetically closed space. The first embodiment described in detail above illustrates the analysis operation in which the processing groove 134 is irradiated with the observation light from the observation window 33 and data is obtained. However, the processing in the processing groove according to this embodiment is not limited to the analysis and detection. For example, after two liquids are agitated in the operation illustrated in FIG. 9, the liquids may be held in the processing groove 134 and caused to react, and then the liquids may be collected from the waste liquid well 14. Alternatively, processing other than the optical measurement, such as control of a temperature while holding a liquid in the processing groove 134 may be performed.

In the configuration according to this embodiment, as illustrated in FIG. 1, the processing liquid feed recess 46, which is the fifth recess, is installed between the processing groove 134 and the downstream bubble removal recess 45, which is the second recess, through the liquid delivery groove. However, the structure is not limited only to this. The configuration in which not only the fifth recess, but also a plurality of recesses is further coupled may be employed. Specifically, the configuration may include at least one recess coupled to the downstream bubble removal recess 45, which is one of the liquid delivery grooves and the second recess, through the membrane 20 which is an elastic membrane, and the processing groove 134 coupled to any one of the at least one recess in one of the liquid delivery grooves through the membrane 20.

In the first embodiment described in detail above, the first groove, which is the upstream bubble eliminating groove, and the second groove, which is the downstream bubble eliminating groove, are used to cause a liquid to flow in a reciprocating motion in the mixing well 13 and two gaps, i.e., the upstream bubble removing portion gap 443 and the downstream bubble removing portion gap 453, and to be agitated, thereby eliminating bubbles in the liquid. In other words, the embodiment described above is also an agitating method for mixing a plurality of liquids. In the agitating method according to this embodiment, the first groove, which is the upstream bubble eliminating groove, and the second groove, which is the downstream bubble eliminating groove, are branched from the mixing vessel; the plurality of liquids is joined into the mixing vessel by using the first groove; after suction of a liquid from the mixing vessel to the first groove is started, suction of a liquid from the mixing vessel to the second groove is started; and after completion of discharge of a liquid from the first groove to the mixing vessel, discharge of a liquid from the second groove to the mixing vessel is completed.

In the first embodiment described above, the pressure to be applied to each recess is switched between two types, i.e., pressurization and decompression, thereby deforming the membrane and performing liquid feeding and sealing. The operation can be performed on the recesses with the same size. However, the size of each recess is set as follows.

In the bubble eliminating structure according to this embodiment, when a liquid is fed from a certain well to another well, three or more recesses are required between the two wells. In FIG. 1, the sample sealing recess 41, which is the fourth recess, the sample liquid feed recess 43, which is the third recess, and the upstream bubble removal recess 44, which is the first recess, are present between the sample well 11 and the mixing well 13, the reagent sealing recess 42, which is the fourth recess, the sample liquid feed recess 43, and the upstream bubble removal recess 44 are present between the reagent well 12 and the mixing well 13, and the downstream bubble removal recess 45, which is the second recess, the processing liquid feed recess 46, which is the fifth recess, and the processing sealing recess 47, which is the sixth recess, are present between the mixing well 13 and the waste liquid well 14.

Among the three recesses as described above, a liquid is substantially fed only to the center recess, i.e., the sample liquid feed recess 43 and the processing liquid feed recess 46. The volume of the recess is equal to the amount of liquid to be fed in one operation. On the other hand, the recesses at both sides of the center recess function as a valve. In the case of sucking a liquid into the center recess, the upstream bubble removal recess 44, which is the downstream-side recess, and the processing sealing recess 47 are pressurized and sealed. In the case of discharging a liquid from the center recess, the sample sealing recess 41, which is the upstream-side recess, the reagent sealing recess 42, and the downstream bubble removal recess 45 are pressurized and sealed. Accordingly, the volume of the recesses at the both sides is irrelevant to the amount of liquid to be fed, and thus the volume of the recesses at the both sides can be reduced as compared with the center recess.

However, since the upstream bubble removal recess 44 and the downstream bubble removal recess 45 are used for bubble removal or agitating operation, the volume of the recesses is limited. Specifically, the total volume of the upstream bubble removal recess 44 and the downstream bubble removal recess 45 needs to be smaller than the amount of the mixture 83 held in the mixing well 13. This is because, as illustrated in FIG. 9(B), when the mixture is sucked into both the upstream bubble removal recess 44 and the downstream bubble removal recess 45, to be more specific, when the mixture is sucked into both the upstream bubble removing gap 443 and the downstream bubble removing gap 445, if the mixture is not left in the mixing well 13, air is sucked, so that new bubbles are contaminated. Therefore, the volume of each recess is desirably greater than or equal to a half of the total amount of liquid held in the mixing well 13.

Figure 11:
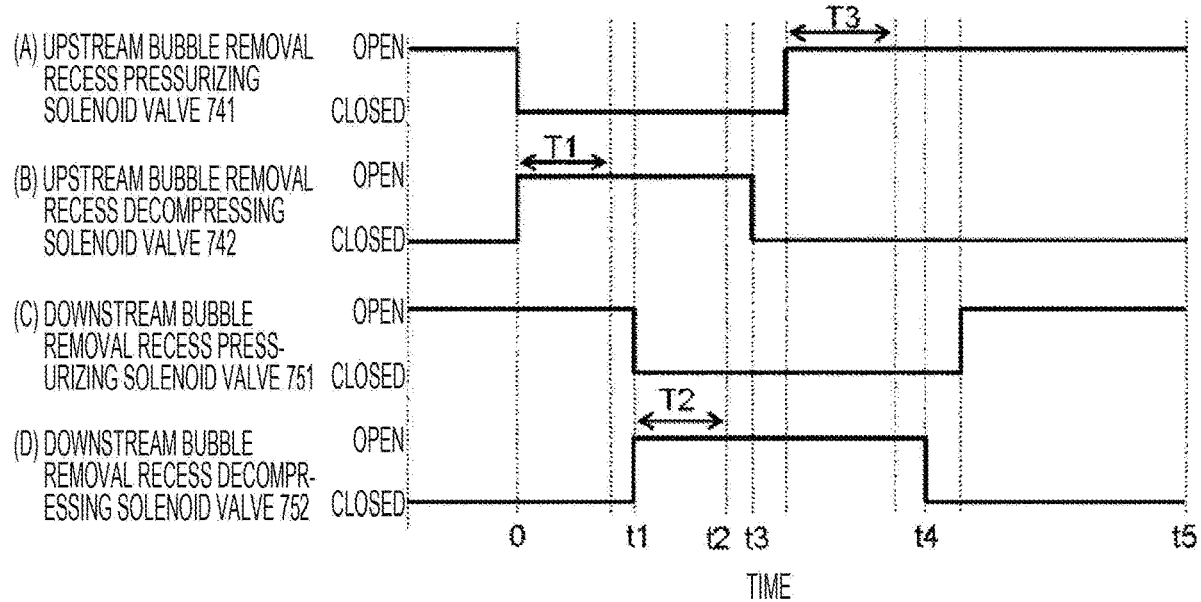
FIG. 11 is an example of a control timing diagram for solenoid valves at the time of bubble removing operation of the chemical analysis device according to the first embodiment.

FIG. 11 is a control timing diagram illustrating the solenoid valves at the time of bubble removing operation in the chemical analysis device according to this embodiment. This timing diagram is the timing diagram for the bubble eliminating method in which the decompressing solenoid valve corresponding to the first recess is brought into the open state to thereby decompress the first recess; after completion of suction of a liquid from the vessel to the first recess, the decompressing solenoid valve corresponding to the second recess is brought into the open state to thereby decompress the second recess; after completion of suction of a liquid from the vessel to the second recess, the decompressing solenoid valve corresponding to the first recess is brought into the closed state, and then the pressurizing solenoid valve corresponding to the first recess is brought into the open state and the first recess is pressurized; and discharge of a liquid from the first recess to the vessel is started.

FIGS. 11(A), 11(B), 11(C), and 11(D) respectively illustrate opening/closing control timings for the upstream bubble removal recess pressurizing solenoid valve 741, the upstream bubble removal recess decompressing solenoid valve 742, the downstream bubble removal recess pressurizing solenoid valve 751, and the downstream bubble removal recess decompressing solenoid valve 752. These control operations are executed in the air pipeline installed in the control portion 60 as described above.

At time 0, the upstream bubble removal recess pressurizing solenoid valve 741 is closed and the upstream bubble removal recess decompressing solenoid valve 742 is opened, thereby sucking the mixture and bubbles to the upstream bubble removal recess 44 side via the upstream bubble eliminating groove 114. Assuming that a time required for completing the suction is represented by T1, well in advance, the downstream bubble removal recess pressurizing solenoid valve 751 is closed and the downstream bubble removal recess decompressing solenoid valve 752 is opened at time t1, thereby sucking the mixture and bubbles to the downstream bubble removal recess 45 side via the downstream bubble eliminating groove 131.

When a time required for completing the suction to the downstream bubble removal recess 45 side is represented by T2 and the suction is completed at time t2, well in advance, the upstream bubble removal recess decompressing solenoid valve 742 is closed at time t3, and discharge of the mixture from the upstream bubble removal recess 44 side to the mixing well 13 is started. In other words, discharge of the mixture from the upstream bubble removal recess 44 side to the mixing well 13 is carried out after the suction to the downstream bubble removal recess 45 side is completed.

Further, the upstream bubble removal recess pressurizing solenoid valve 741 is opened, and the mixture and bubbles are completely returned from the upstream bubble removal recess 44 side to the mixing well 13. Assuming that a time required for the mixture and bubbles to be completely returned is represented by T3, well in advance, the downstream bubble removal recess decompressing solenoid valve 752 is closed at time t4, and discharge of the mixture from the downstream bubble removal recess 45 side to the mixing well 13 is started. In other words, discharge of the mixture from the downstream bubble removal recess 45 side to the mixing well 13 is carried out after bubbles are returned from the upstream bubble removal recess 44 side to the mixing well 13. Furthermore, the downstream bubble removal recess pressurizing solenoid valve 751 is opened and the mixture is completely returned from the downstream bubble removal recess 45 side to the mixing well 13, and then bubbles are moved to the upper portion of the mixing well 13.

In this manner, the mixture is returned to the mixing well 13, the same bubble removing operation is repeated by setting the time up to time t5 when the movement of bubbles is completed as one cycle, thereby making it possible to perform bubble removal as well as agitation.

That is, according to the bubble eliminating structure, the bubble eliminating method, and the agitating method according to the first embodiment described in detail above, it is possible to eliminate bubbles in a liquid by simply agitating the liquid and to perform agitation.

Next, a modified example of the control timing diagram for the solenoid valves at the time of bubble removing operation according to this embodiment will be described. In the bubble eliminating structure and the chemical analysis device according to this embodiment, if the recesses used for bubble removal, such as the upstream bubble removal recess 44 and the downstream bubble removal recess 45, cannot be downsized, the control timing of the bubble removing operation illustrated in FIG. 12 may be changed. This timing diagram is the timing diagram for the bubble eliminating method in which the decompressing solenoid valve corresponding to the first recess is brought into the open state and the first recess is decompressed. After the suction of a liquid from the vessel to the first recess is started, the decompressing solenoid valve corresponding to the second recess is brought into the open state and the decompression of the second recess is started. Before completion of suction of a liquid from the vessel to the second recess, the decompressing solenoid valve corresponding to the first recess is brought into the closed state.

Figure 12:
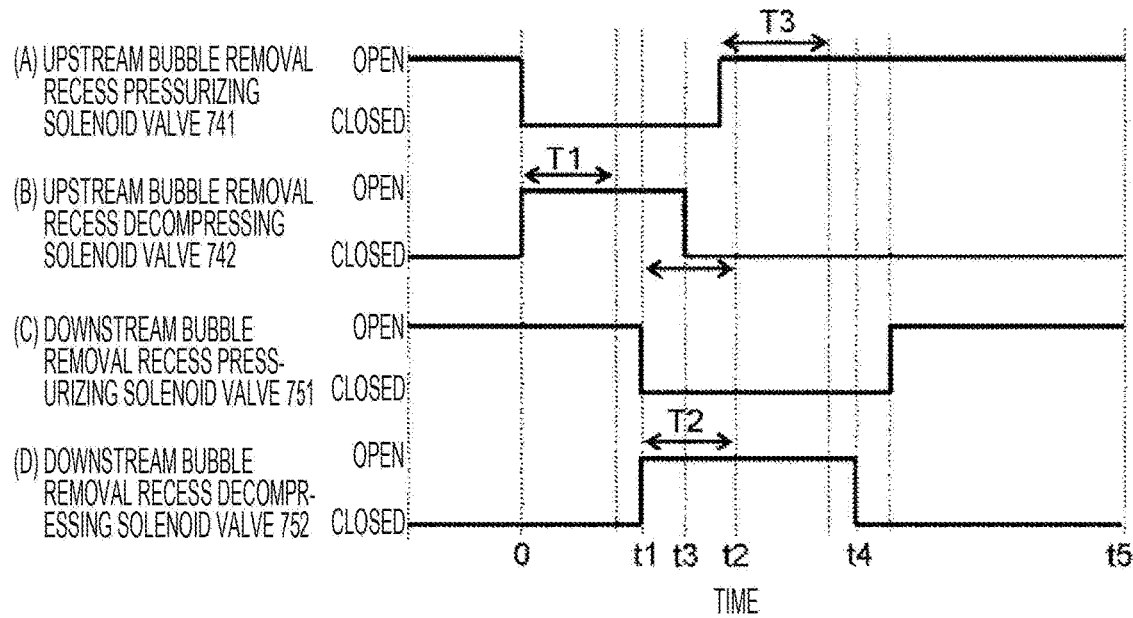
FIG. 12 is a diagram illustrating a modified example of the control timing diagram for the solenoid valves at the time of the bubble removing operation of the chemical analysis device according to the first embodiment.

The bubble removing operation illustrated in FIG. 12 assumes a case where the total volume of the upstream bubble removal recess 44 and the downstream bubble removal recess 45 is larger than the amount of the mixture. Like FIG. 11, FIGS. 12(A), 12(B), 12(C), and 12(D) respectively illustrate opening/closing control timings for the upstream bubble removal recess pressurizing solenoid valve 741, the upstream bubble removal recess decompressing solenoid valve 742, the downstream bubble removal recess pressurizing solenoid valve 751, and the downstream bubble removal recess decompressing solenoid valve 752.

At time 0, the upstream bubble removal recess pressurizing solenoid valve 741 is closed and the upstream bubble removal recess decompressing solenoid valve 742 is opened, thereby sucking the mixture and bubbles to the upstream bubble removal recess 44 side. Assuming that a time required for completing the suction is represented by T1, well in advance, the downstream bubble removal recess pressurizing solenoid valve 751 is closed and the downstream bubble removal recess decompressing solenoid valve 752 is opened at time t1, thereby sucking the mixture and bubbles to the downstream bubble removal recess 45 side. The operation described above is the same as the operation illustrated in FIG. 11.

When a time required for completing the suction to the downstream bubble removal recess 45 side is represented by T2 and the suction is completed at time t2, the suction is performed at both the upstream bubble removal recess 44 side and the downstream bubble removal recess 45 side at time t2. As a result, the mixture is not left in the mixing well 13 and air is sucked at the downstream bubble removal recess 45 side.

Accordingly, in the modified example illustrated in FIG. 12, at time t3 which is earlier than time t2, the upstream bubble removal recess decompressing solenoid valve 742 is closed and discharge of the mixture from the upstream bubble removal recess 44 side to the mixing well is started. In other words, the discharge of the mixture from the upstream bubble removal recess 44 side to the mixing well 13 is carried out before the suction to the downstream bubble removal recess 45 side is completed. In this manner, the discharge operation from the upstream bubble removal recess 44 side to the mixing well 13 is accelerated, thereby preventing the mixture from being removed from the mixing well 13.

The subsequent operation is the same as the operation illustrated in FIG. 11. Specifically, the upstream bubble removal recess pressurizing solenoid valve 741 is opened to completely return the mixture and bubbles to the mixing well 13 from the upstream bubble removal recess 44 side. Assuming that a time required for the mixture and bubbles to be completely returned is represented by T3, well in advance, the downstream bubble removal recess decompressing solenoid valve 752 is closed at time t4, and discharge of the mixture from the downstream bubble removal recess 45 side to the mixing well 13 is started. In other words, discharge of the mixture from the downstream bubble removal recess 45 side to the mixing well 13 is carried out after bubbles are returned from the upstream bubble removal recess 44 side to the mixing well 13.

Further, the downstream bubble removal recess pressurizing solenoid valve 751 is opened and the mixture is completely returned from the downstream bubble removal recess 45 side to the mixing well 13, thereby moving bubbles to the upper portion of the mixing well 13. The same bubble removing operation is repeated by setting the time up to time t5 when the mixture is returned to the mixing well 13 and the movement of bubbles is completed as one cycle.

In this modified example, time t3 when the discharge of the mixture from the upstream bubble removal recess 44 side to the mixing well 13 is started is required to be earlier than time t2 when the suction to the downstream bubble removal recess 45 side is completed. Further, the discharge from the upstream bubble removal recess 44 side can be started earlier than time t1 when the suction to the downstream bubble removal recess 45 side is started. However, there is a possibility that the suction to the upstream bubble removal recess 44 side has not been completed yet, which leads to a deterioration in the efficiency of the bubble elimination operation. For this reason, time t3 when the discharge of the mixture from the upstream bubble removal recess 44 side to the mixing well is started is desirably set between time 1 when the suction to the downstream bubble removal recess 45 side is started and time t2 when the suction to the downstream bubble removal recess 45 side is completed.

In particular, when the discharge from the upstream bubble removal recess 44 side is started at time 1 when the suction to the downstream bubble removal recess 45 side is started, most of the mixture is directly moved from the upstream bubble removal recess 44 side to the downstream bubble removal recess 45 side without passing through the mixing well 13. Also, in this case, when bubbles that are first located at the bottom surface portion of the mixing well 13 are moved to the downstream bubble removal recess side, the bubbles are moved in the last part of the mixture. Then, when the mixture is discharged from the downstream bubble removal recess 45 side to the mixing well 13, the bubbles are moved in the first part of the mixture and are further moved to the upper part of the mixing well 13 and thus are more likely to disappear.

In this manner, time t3 when the discharge of the mixture from the upstream bubble removal recess 44 side to the mixing well 13 is started is set to be earlier than time t2 when the suction from the mixing well 13 to the downstream bubble removal recess 45 side is completed. Consequently, bubbles can be eliminated and the time for bubbles removal can be reduced even when the total volume of the upstream bubble removal recess 44 and the downstream bubble removal recess 45 is larger than the amount of the mixture.

Specifically, if time t3 is set to be earlier than time t2 as illustrated in FIG. 12, the time for bubble removal can be reduced and the overall analysis operation can be speeded up, as compared with the case of the first embodiment in which, as illustrated in in FIG. 11, after time t2 when the suction from the mixing well 13 to the downstream bubble removal recess 45 side is completed, the discharge of the mixture from the upstream bubble removal recess 44 side to the mixing well 13 is started at time t3.

Note that in the air pipeline diagram illustrated in FIG. 3, the air pipe is branched into two lines from each solenoid valve and is connected to two driving portions. Accordingly, the same operation can be carried out simultaneously on the two driving portions. This is an example of a configuration for carrying out the same analysis on two samples. However, if different analysis are carried out, solenoid valves may be disposed in the middle of a route in which the air pipe is branched into two lines to be connected to the driving portions, and driving of the individual driving portions may be executed.

According to the present invention described in detail above, the bubble eliminating structure, the bubble eliminating method, and the agitating method can eliminate bubbles in a liquid by agitating the liquid with a simple configuration, and can also perform agitation. Furthermore, it is possible to reduce a time for bubble removal and to increase the speed for analysis.

Note that the present invention is not limited to the embodiments described above, but also includes various modified examples. For example, the embodiments are described in detail to facilitate the explanation of the present invention, and are not limited to the configuration including all the components described above. A part of the configuration according to a certain embodiment can be replaced by the configuration according to another embodiment. Further, the configuration according to another embodiment may be added to the configuration according to a certain embodiment. Furthermore, addition, deletion, and replacement of other structures can be made for a part of the configuration according to each embodiment.

REFERENCE SIGNS LIST

10 analysis chip
11 sample well
12 reagent well
13 mixing well
14 waste liquid well
111, 112, 113, 114, 121, 122, 131, 132, 133, 134, 135, 136 groove
20 membrane
30 lid
31 rotary supporting portion
32 injection window
33 observation window
40 driving portion
41, 42, 43, 44, 45, 46, 47 recess
411, 421, 431, 441, 451, 461, 471 pressurizing pipe
412, 422, 432, 442, 452, 462, 472 decompression pipe
50 housing
51 lock mechanism
60 control portion
61 operating portion
70 air pipe
71 pressurizing pump
711, 721, 731, 741, 751, 761, 771 pressurizing solenoid valve
72 decompressing pump
712, 722, 732, 742, 752, 762, 772 decompressing solenoid valve

The invention claimed is:

1. A bubble eliminating method using a bubble eliminating structure, the bubble eliminating structure including an analysis chip installed on an upper surface side of an elastic membrane, and a driving portion installed on a lower surface side of the elastic membrane, the analysis chip including a vessel provided on an upper surface of the analysis chip, and a first groove and a second groove that are provided on a lower surface of the analysis chip and are branched from the vessel, the bubble eliminating method comprising:

holding a liquid in the vessel;
starting suction of the liquid from the vessel into the first groove;
starting suction of the liquid from the vessel into the second groove after the starting of the suction of the liquid from the vessel into the first groove, while a portion of the liquid remains in the vessel;
discharging the liquid from the first groove into the vessel; and
discharging the liquid from the second groove into the vessel after completion of the discharging of the liquid from the first groove into the vessel.

2. The bubble eliminating method according to claim 1, wherein the driving portion includes a plurality of recesses provided on the upper surface of the driving portion, the plurality of recesses including a first recess and a second recess that are coupled to the first groove and the second groove, respectively, through the elastic membrane, a third recess coupled to the first recess, and a fourth recess coupled to the third recess,
the method further comprising:
decompressing the third recess while the first recess is pressurized;
after the third recess is decompressed while the first recess is pressurized, pressurizing the third recess while the pressurizing the fourth recess.

3. The bubble eliminating method according to claim 1, further comprising:
repeatedly suctioning the liquid into the first groove and the second groove and discharging the liquid from the first groove and the second groove.

4. The bubble eliminating method according to claim 1, wherein
the driving portion includes a plurality of recesses provided on the upper surface of the driving portion, the plurality of recesses including a first recess and a second recess that are coupled to the first groove and the second groove, respectively, through the elastic membrane,
the method further comprising:
after the first recess is decompressed to start suction of a liquid from the vessel into the first groove, the second recess is decompressed to start suction of a liquid from the vessel into the second groove, and
after the first recess is pressurized to complete suction of a liquid from the first groove into the vessel, the second recess is pressurized to complete discharge of a liquid from the second groove into the vessel.

5. The bubble eliminating method according to claim 4, further comprising:
controlling an open state and a closed state of each of a pressurizing solenoid valve and a decompressing solenoid valve that correspond to the first recess and the second recess, respectively to perform decompression and pressurization of the first recess and the second recess.

6. The bubble eliminating method according to claim 5, further comprising:
opening the decompressing solenoid valve corresponding to the first recess to the open state to decompress the first recess and generating a gap between the elastic membrane and the analysis chip,
after completion of suction of the liquid from the vessel into the first recess, opening the decompressing solenoid valve corresponding to the second recess to the open state to decompress the second recess and generating a gap between the elastic membrane and the analysis chip, and
after completion of suction of the liquid from the vessel into the second recess, the decompressing solenoid valve corresponding to the first recess is brought into the closed state.

7. The bubble eliminating method according to claim 6, further comprising:
after the decompressing solenoid valve corresponding to the first recess is brought into the closed state, opening the pressurizing solenoid valve corresponding to the first recess to the open state thereby pressurizing the first recess.

8. The bubble eliminating method according to claim 5, further comprising:
opening the decompressing solenoid valve corresponding to the first recess is to the open state to decompress the first recess and generating a gap between the elastic membrane and the analysis chip,
after suction of the liquid from the vessel into the first recess is started, opening the decompressing solenoid valve corresponding to the second recess to the open state to start decompression of the second recess and generating a gap between the elastic membrane and the analysis chip, and
before completion of suction of the liquid from the vessel into the second recess, closing the decompressing solenoid valve corresponding to the first recess to the closed state.

* * * * *